United States Patent
Heikki et al.

(10) Patent No.: US 10,780,157 B2
(45) Date of Patent: *Sep. 22, 2020

(54) MULTI-CBV VACCINE FOR PREVENTING OR TREATING TYPE I DIABETES

(71) Applicant: Vactech Oy, Tampere (FI)

(72) Inventors: Hyöty Heikki, Tampere (FI); Mikael Knip, Helsinki (FI); Olli Laitinen, Tampere (FI); Outi Tolonen, Oulu (FI); Minna Pulkki, Tampere (FI); Sami Oikarinen, Tampere (FI); Hanna-Riikka Honkanen, Hyllykallio (FI); Valérie Lecouturier, Chazay d'Azergues (FR); Jeffrey Almond, Dardilly (FR); Malin Flodström-Tullberg, Nykoping (SE)

(73) Assignee: Vactech Oy, Tampere (FI)

( * ) Notice: Subject to any disclaimer, the term of this patent is extended or adjusted under 35 U.S.C. 154(b) by 0 days.

This patent is subject to a terminal disclaimer.

(21) Appl. No.: 16/265,681

(22) Filed: Feb. 1, 2019

(65) Prior Publication Data
US 2020/0000908 A1    Jan. 2, 2020

Related U.S. Application Data

(63) Continuation of application No. 15/465,854, filed on Mar. 22, 2017, now Pat. No. 10,258,685, which is a continuation of application No. 14/352,585, filed as application No. PCT/EP2012/070653 on Oct. 18, 2012, now abandoned.

(30) Foreign Application Priority Data

Oct. 18, 2011 (EP) .................................... 11306344

(51) Int. Cl.
| | | |
|---|---|---|
| A61K 39/125 | (2006.01) | |
| A61K 39/12 | (2006.01) | |
| C07K 16/10 | (2006.01) | |
| A61K 39/13 | (2006.01) | |
| A61K 39/39 | (2006.01) | |
| A61K 39/00 | (2006.01) | |

(52) U.S. Cl.
CPC ............ *A61K 39/125* (2013.01); *A61K 39/12* (2013.01); *A61K 39/13* (2013.01); *A61K 39/39* (2013.01); *C07K 16/1009* (2013.01); *A61K 2039/505* (2013.01); *A61K 2039/5252* (2013.01); *A61K 2039/5258* (2013.01); *A61K 2039/53* (2013.01); *A61K 2039/55* (2013.01); *A61K 2039/58* (2013.01); *C12N 2770/32334* (2013.01)

(58) Field of Classification Search
None
See application file for complete search history.

(56) References Cited

U.S. PATENT DOCUMENTS

| | | | |
|---|---|---|---|
| 10,258,685 B2 * | 4/2019 | Heikki | ............ A61K 39/12 |
| 2010/0047273 A1 | 2/2010 | Rappuoli et al. | |
| 2012/0177686 A1 | 7/2012 | Oerter | |

FOREIGN PATENT DOCUMENTS

| | | |
|---|---|---|
| WO | WO 2001/000236 | 1/2001 |
| WO | WO 2011/009854 | 1/2011 |

OTHER PUBLICATIONS

Honeyman et al., Molecular Medicine, 1995, 1(5):576-582. (Year: 1995).*
Bauer et al., European Journal of Pediatrics 161:491-493, 2002.
Cabrera-Rode, E. et al., "Type 1 diabetes islet associated antibodies in subjects infected by echovirus 16," Diabetologia (2003) 46:1348-1353.
Dotta, Francesco et al., "Coxsackie B4 virus infection of beta cells and natural killer cell insulitis in recent-onset type 1 diabetic patients," Proceedings of the National Academy of Sciences of the United States of America, vol. 104, No. 12, Mar. 2007, pp. 5115-5120.
Elfving M et al., "Maternal Enterovirus infection during Pregnancy as a Risk Factor in Offspring Diagnosed with Type 1 Diabetes between 15 and 30 years of Age," Experimental Diabetes Research, Hindawi Publishing Corporation, US, vol. 2008, Jan. 1, 2008, pp. 1-6.
European Search Report dated Jul. 11, 2012 of European Application No. 11306344.0-2406.
Flodstrom, M. et al., "Diabetogenic Potential of Human Pathogens Uncovered in Experimentally Permissive Beta-Cells," Diabetes, vol. 52, Aug. 2003, pp. 2025-2034.
Flodstrom, M. et al., "Target cell defense prevents the development of diabetes after viral infection," Nature Immunology, vol. 3, No. 4, Apr. 2002, pp. 373-382.
Hindersson, M. et al., "Simultaneous type 1 diabetes onset in mother and son coincident with an enteroviral Infection," Journal of Clinical Virology 33 (2005) 158-167.
Horwitz, M. et al., "Diabetes induced by Coxsackie virus: Initiation by bystander damage and not molecular mimicry," Nature Medicine, vol. 4, No. 7, Jul. 1998, pp. 781-785.
International Search Report and Written Opinion of International Application No. PCT/EP2012/070653 filed Oct. 18, 2012 dated Dec. 14, 2012.
Klemola, Paivi et al., "Diabetogenic effects of the most prevalent enteroviruses in Finnish sewage," New York Academy of Sciences, Annals, Wiley-Blackwell Publishing, Inc., US, vol. 1150, Dec. 1, 2008, pp. 210-212.

(Continued)

*Primary Examiner* — Stacy B Chen
(74) *Attorney, Agent, or Firm* — Bozicevic Field & Francis, LLP

(57) ABSTRACT

The invention is directed to a vaccine comprising: i) coxsackie B virus CBV1 and CBV2, and ii) at least one coxsackie B virus selected from CBV3, CBV4, CBV5 and CBV6. The CBVs are present in the vaccine in inactivated form, in the form of a component of the virus or as an antibody against the virus. The vaccine is effective in preventing and treating type 1 diabetes. So is an anti-coxsackie B virus composition provided.

9 Claims, 6 Drawing Sheets

(56) References Cited

OTHER PUBLICATIONS

Landau B J et al., "Induction of heterotypic virus resistance in adult inbred mice immunized with a variant of Coxsackievirus B3," Microbial Pathogenesis, Academic Press Limited, New York, NY, US, vol. 8, No. 4, Apr. 1, 1990, pp. 289-298.
Lee, et al., "Molecular characterization of enteroviruses isolated from patients with aseptic meningitis in Korea, 2005," Arch Virol (2007) 152:963-970.
Lukashev, Abstract, Reviews in Medical Virology, 2005.
Lukashev, Alexander N., "Role of recombination in evolution of enteroviruses," Rev. Med. Virol., 2005, 15:157-167.
Mariah. et al. "Simultaneous type 1 diabetes onset in mother and son coincident with an enteroviral infection," Journal of Clinical Virology, Elsevier, Amsterdam, NL., 33 (2005) pp. 158-167.
Merikukka, M. et al., "Differences in incidence and co-occurrence of vaccine and nonvaccine human papillomavirus types in Finnish population before human papillomavirus mass vaccination suggest competitive advantage for HPV33," Int. J. Cancer: 128, 1114-1119 (2011).
Nanto-Salon EN, K. et al., "Nasal insulin to prevent type 1 diabetes in children with HLA genotypes and autoantibodies conferring increased risk of disease: a double-blind, randomised controlled trial," Lancet, 2008, 372:1746-55.
Nasri, D. et al., "Typing of Human Enterovirus by Partial Sequencing of VP2," Journal of Clinical Microbiology, Aug. 2007, vol. 45, No. 8, pp. 2370-2379.
Nix et al., "Sensitive, Seminested PCR Amplification of VP1 Sequences for Direct Identification of All Enterovirus Serotypes from Original Clinical Specimens," Journal of Clinical Microbiology, Aug. 2006, vol. 44, No. 8, pp. 2698-2704.
P. Ylipaasto et al., "Enterovirus infection in human pancreatic islet cells, islet tropism in vivo and receptor involvement in cultured islet beta cells," Diabetologia, vol. 47, No. 2, Feb. 1, 2004, pp. 225-239.
Sadeharju, K. et al., "Maternal Antibodies in Breast Milk Protect the Child From Enterovirus Infections," Pediatrics, vol. 119, No. 5, May 2007, pp. 940-947.
See et al., Antimicrobial Agents and Chemotherapy, 37:1593-1598, 1993.
See, Darryl M. et al., "Efficacy of a polyvalent inactivated-virus vaccine in protecting mice from infection with clinical strains of group B coxsackieviruses," Scandinavian Journal of Infectious Diseases, vol. 26, No. 6, 1994, pp. 739-747.
Skyler, Jay, Diabetes Care, Jun. 2015, 38:997-1007.
Stone, Virginia M. et al. (2017) "A Coxsackievirus B Vaccine Protects Against Virus-Induced Diabetes in an Experimental Mouse Model of Type 1 Diabetes", Diabetologia, 6 pages.
Williams, C.H. et al., "Molecular Analysis of an Echovirus 3 Strain Isolated from an Individual Concurrently with Appearance of Islet Cell and IA-2 Autoantibodies," Journal of Clinical Microbiology, Feb. 2006, vol. 44. No. 2, pp. 441-448.
Yoon, J. et al., Virus-Induced Diabetes Mellitus, The New England Journal of Medicine, May 24, 1979, vol. 300, No. 21, pp. 1173-1179.
Zipris, "Epidemiology of type 1 diabetes and what animal models teach us about the role of viruses in disease mechanisms," Clinical Immunology (2009) 131, pp. 11-23.

\* cited by examiner

Maternal vs. child's CBV1 antibodies

US 10,780,157 B2

MULTI-CBV VACCINE FOR PREVENTING OR TREATING TYPE I DIABETES

CROSS REFERENCE

This application is a continuation of U.S. patent application Ser. No. 15/465,854, filed Mar. 22, 2017, which is a continuation of U.S. patent application Ser. No. 14/352,585, filed Apr. 17, 2014, abandoned, which is a national stage filing under 35 U.S.C. § 371 of PCT/EP2012/070653, which claims priority to EP 11306344.0, filed Oct. 18, 2011, which applications are incorporated by reference herein in their entirety.

FIELD OF THE INVENTION

The present invention relates to anti-viral compositions e.g. vaccines and methods useful in preventing or treating type 1 diabetes. More particularly the invention relates to a vaccine comprising enteroviruses, components thereof and/or antibodies thereto.

BACKGROUND OF THE INVENTION

Type 1 diabetes (T1D) is a severe disease that has become more and more frequent already at a very early age. In type 1 diabetes the beta-cells of the pancreas are destroyed, which leads to insulin deficiency. The destruction of the beta-cells is believed to be caused by an autoimmune response, which in turn is assumed to be induced by a virus infection.

The connection between enteroviruses and T1D has been documented in a multitude of studies. Enteroviruses have been detected in the pancreas, blood and intestinal mucosa of patients with T1D more frequently than in control subjects and prospective studies have supported their role in the initiation of the beta-cell damaging process associated with T1D. Enteroviruses infect pancreatic beta-cells in cell culture and cause diabetes in animal models. Enterovirus vaccines have therefore been suggested for preventing T1D. However, the knowledge of which enterovirus serotypes that are involved in the disease is limited.

The group of enteroviruses includes more than 100 different serotypes, and because a vaccine covering all the 100 enterovirus serotypes is not realistic using the current standard vaccine technologies, the knowledge of which serotypes are involved in T1D is critical for vaccine development. Enterovirus infections are usually subclinical, but they may also cause various kinds of diseases. For example polioviruses, coxsackie B virus (CBV), coxsackie A virus (CAV), and echovirus as well as numbered enteroviruses are enteroviruses known to be involved in the development of a variety of diseases. For example Lee et al., 2007, Arch Virol, 152:963-970 analyzed clinical isolates from aseptic meningitis patients, and found that CBV5 was the most predominant strain. In addition CBV1, CBV3 and echovirus 9 were identified.

The spectrum of responsible serotypes varies a lot from disease to disease, and even in one disease like T1D the exact serotypes have not been fully and reliably identified. Indeed, previous studies reporting association between enteroviruses and T1D were not able to discriminate between serotype or were restricted to case reports. Some studies have suggested that a particular CBV serotype may be important (Yoon et al, 1979 New Eng J of Med, v300, p1173; Hindersson M, et al., 2005, J Clin Virol v.33 p158; Dotta F. et al., 2007, PNAS 104: 5115; US2010/0047273 (Rappuoli et al.)). However, other than CBV enteroviruses have also been sporadically reported (Cabrera-Rode et al., 2003, Diabetologia; Williams et al., 2006, J Clin Micro v.44 p441).

Klemola et al., 2008, Immunology of Diabetes V: Ann. N.Y. Acad. Sci 1150:210-212 analyzed sewage samples for non-polio enteroviruses. The most commonly detected serotypes were CBV1-5, Echo 6, 7, 11, 25 and 30. They were tested for islet tropism. All serotypes were found to be destructive. No evidence suggesting that only certain enterovirus serotypes should be considered potentially diabetogenic was found.

WO01/00236 (Hyöty et al.) suggests the use of oral poliovirus in a vaccine against T1D. In addition it suggests another diabetes vaccine comprising one or more inactivated non-polio enteroviruses selected from the group consisting of CBV serotypes 1, 2, 3, 4, 5 and 6, echovirus serotypes 3, 4, 6, 9, 11, 22 and 30, CAV serotypes 9 and 16. However, no data is given as to the role of the individual serotypes listed. The immune response obtained by OPV, which is a live attenuated vaccine was believed to induce a T-cell mediated cross-reactive immune response, whereas the inactivated vaccine was believed to be serotype specific.

Despite a lot of investigation, there is still a great need for developing effective means and methods for preventing and treating type 1 diabetes. Embodiments of the present invention meet these needs.

SUMMARY OF THE INVENTION

The present invention is based on the finding that the whole coxsackie B virus (CBV) group may induce type 1 diabetes (T1D). Preliminary tests showed that CBV1 and CBV2 were clear risk serotypes, whereas CBV3, CBV4, CBV5 and CBV6 seemed to reduce the risk of the disease. The invention resides in the surprising finding that an even more effective vaccine against T1D should include not only those CBVs that show a high risk for inducing the disease, but also those serotypes that appear neutral or even protective against T1D.

In addition, an antibody-mediated cross-reaction was found between the different CBV serotypes. This finding makes it feasible to use antibody-inducing vaccines i.e. vaccines comprising inactivated viruses, or components thereof. These vaccines are safer than attenuated live vaccines, but still very effective. Alternatively the vaccine may already contain antibodies against the CBVs.

The present invention is directed to a vaccine comprising: i) coxsackie B virus CBV1 and CBV2 in inactivated form or in the form of a component of said virus, and ii) at least one coxsackie B virus selected from the group consisting of CBV3, CBV4, CBV5 and CBV6 in inactivated form or in the form of a component of said virus.

The present invention is also directed to a composition e.g. a vaccine comprising: i) antibodies against coxsackie B virus CBV1 and CBV2, and ii) antibodies against at least one coxsackie B virus selected from the group consisting of CBV3, CBV4, CBV5 and CBV6.

The present invention is further directed to said vaccines for use in preventing or treating type 1 diabetes.

Still further the invention is directed to an anti-coxsackie B virus composition for use in treating or preventing type 1 diabetes.

A method for preventing or treating type 1 diabetes in a subject in need thereof comprising administering to the subject a vaccine comprising: i) coxsackie B virus CBV1 and CBV2 in inactivated form or in the form of a component of said virus, and ii) at least one coxsackie B virus selected from the group consisting of CBV3, CBV4, CBV5 and CBV6 in inactivated form or in the form of a component of said virus is described.

A method for preventing or treating type 1 diabetes in a subject in need thereof comprising administering to the subject a vaccine comprising: i) antibodies against coxsackie B virus CBV1 and CBV2, and ii) antibodies against at least one coxsackie B virus selected from the group consisting of CBV3, CBV4, CBV5 and CBV6 is also described.

Further a method for preventing or treating type 1 diabetes in a subject in need thereof comprising administering to the subject an anti-coxsackie B virus (anti-CBV) composition is described.

Some specific embodiments of the invention are set forth in the dependent claims.

DETAILED DESCRIPTION OF THE INVENTION

Figure 1:
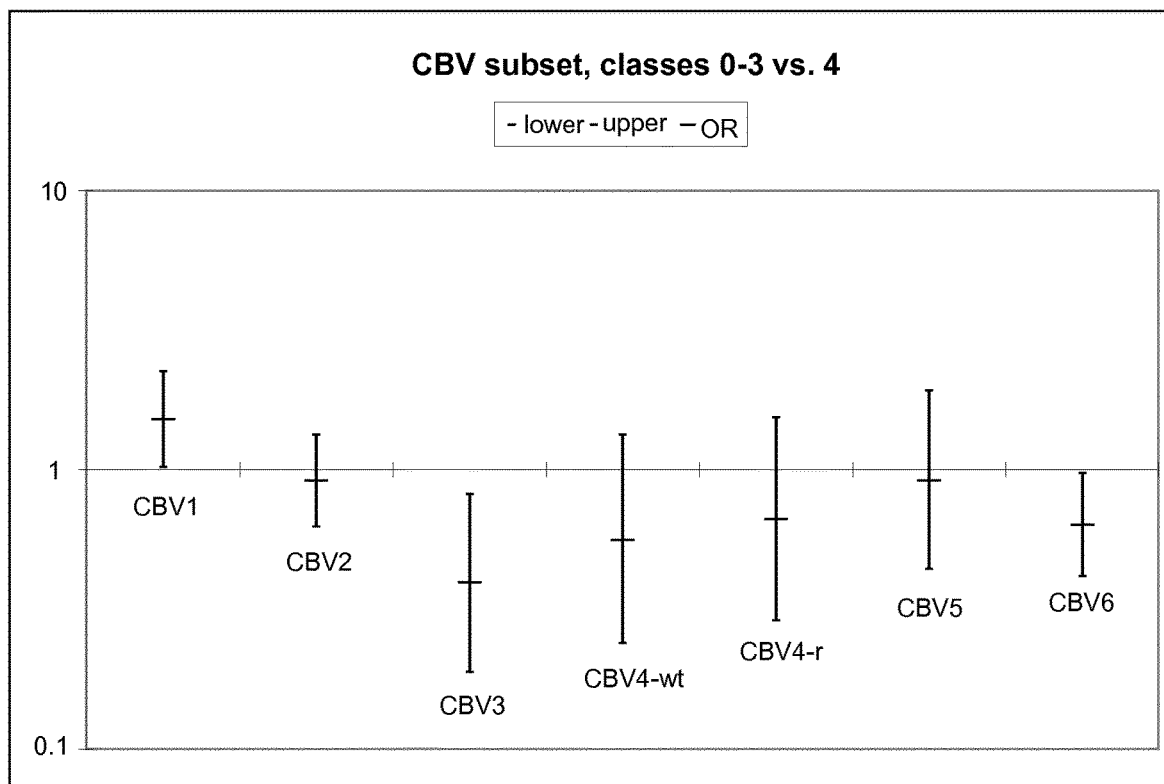
FIG. 1 shows the OR and CI values, and the prevalence of antibodies for the CBV serotypes.
Figure 1:
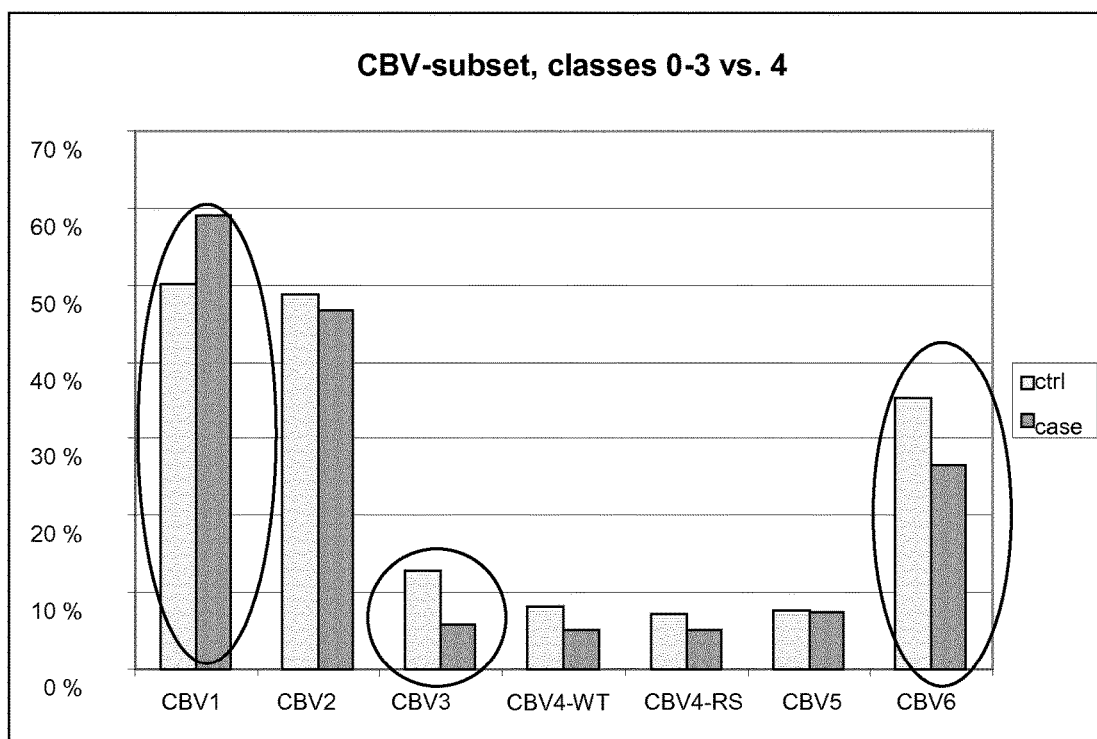

The present invention is based on the new finding that all six different coxsackie B group viruses (CBVs) can be potential risk viruses for type 1 diabetes (T1D) and therefore all the CBVs may be included into a vaccine. This kind of vaccine is optimal for the prevention of T1D. Each CBV serotype included in the vaccine will also give protection against not only the homotypic virus type but also cross-protection against the other CBV types.

There are six genetically and structurally closely related CBV serotypes that are the only known enteroviruses to use the cellular receptor CAR to enter the target cell. CAR is expressed on human insulin-producing beta cells in the pancreas and all CBVs productively infect beta cells in vitro. The six CBVs can induce inter-serotype cross-protection. Since the six serotypes are the only enteroviruses to use CAR, they may share some specific characteristics, either in terms of antigenicity or in terms of tropism.

There are recognized risk viruses such as CBV1 and CBV2 that were associated with increased risk of T1D in virus antibody screening study (causative viruses). In addition, certain other CBV serotypes such as CBV3 and CBV6 were associated with decreased risk of T1D (protective effect) in these analyses. In additional analyses, the presence of the CBV group viruses in serum was associated with increased risk of T1D suggesting that all CBV viruses can have diabetogenic potential. The diabetogenic potential may be first determined by the ability to infect beta cells. It may then be linked to any CBV serotypes and the pathogenicity may be modulated by genetic mutations in CBV strains and recombinations which are known to occur between CBV serotypes circulating in a given population. Such serotype and strain-specific modulation of pathogenicity has been observed for polioviruses. All three serotypes can cause poliomyelitis because they are the only enteroviruses to use PVR as their receptor, however PV2 was generally less pathogenic than PV1, and furthermore, for each serotypes, some strains (e.g. the vaccine strains Sabin) showed a very weak pathogenicity.

In one population few CBV serotypes may predominate as diabetogenic viruses such as CBV1 and CBV2 in the Finnish population in the present study, while other CBV serotypes may have a much weaker diabetogenic effect. The viruses with a weaker diabetogenic potential would then appear protective due to their ability to induce immunological cross-protection against more diabetogenic CBV serotypes.

A virus may also be diabetogenic in one part of a population but either protective or neutral in another part of the same population. Such phenomenon can be based for example on the different genetical make-up of different subpopulations such as differences in HLA, MDA-5 or other immunologically important genotypes. One of the clearest genetics driven population dividing characteristic is the sex, and therefore different risk, neutral or protective characters may be observed for a serotype when its influence is studied separately in females and males. The protective and risk character may also depend on the time of infection. The later the time window is the more risk character the virus shows, On the other hand, the infections at a very early age, without protection provided by maternal antibodies, can be extremely risky.

There are certain scenarios, by which the neutral or even protective virus types can turn into risk viruses or certain risk viruses can be replaced with other ones:

An example of such a process is provided by polioviruses (belonging to the enteroviruses). In this case the live attenuated vaccine strains induce an immunological response against its wild-type predecessor. In some rare cases the attenuated vaccine strains can revert back to the disease causing form and therefore it represents a mild risk for the disease. Such strain can therefore be called "vaccine-derived poliovirus" (VDPV). Inter-serotype recombination is a mechanism that may lead to emergence of new risk viruses. This can occur between genetically related serotypes and it is a relatively common phenomenon especially among closely related enteroviruses (Vopr Virusol. 2005 May-June; 50(3):46-52). A special character of the CBVs is that they all use the CAR receptor and infect pancreatic beta-cells in vitro. The serological properties and receptor binding characteristics of CBVs are determined by their structural capsid proteins, the receptor binding characteristic being crucial for the cellular tropism. However, the infection dynamics or virulence is mainly determined by other regions of the CBV genome; for the latter ones the special importance are 5' and 3'-non-coding regions (NCRs) as well as non-structural protein encoding regions. Recombinations between enteroviruses occur usually between so-called hot-spots, which lie in the enterovirus genome between the 5'-NCR and structural proteins and between structural proteins and a non-structural protein. Therefore, inter-serotype recombination can lead to mixing of the serological and receptor binding properties of one strain with "pathological" properties of another enterovirus strain. Thus a multi-CBV vaccine will have a crucial role in preventing this type of development among enteroviruses associated with T1D. "Multi-CBV vaccine" refers to a vaccine directed to more than one CBV serotype.

In HPV studies it has been found that when the strongest risk strains are eliminated from the human populations by vaccination the released niche can be occupied by other disease causing strains (Int J Cancer. 2011 Mar. 1; 128(5): 1114-9. doi: 10.1002/ijc.25675. Epub 2010 Nov. 28.). A similar phenomenon can occur if the strongest CBV risk serotypes are eliminated by vaccination. In such populations where the strong risk serotypes are rare this can also occur naturally.

In view of the above, it is reasonable to include many or all of the six CBV serotypes into the same vaccine in order to guarantee its maximal efficiency in terms of immune protection against diabetogenic enteroviruses.

The vaccine of the invention comprises the CBVs in inactivated form, and/or it comprises components of the viruses, and/or antibodies against said viruses. In addition to the inactivated CBV1 and CBV2, components thereof, or antibodies thereto, the vaccine contains at least one, two, three or four of CBV3, CBV4, CBV5 and CBV6, components thereof, or antibodies thereto in any combination. Due to the antibody-mediated cross-reactivity found between the CBVs, a protective effect against a missing serotype may also be obtained. However, in a preferred embodiment the vaccine is a "pan-CBV vaccine", which means that it is directed against all six serotypes, i.e. it comprises inactivated CBV1, CBV2, CBV3, CBV4, CBV5, and CBV6, and/or components of said six CBVs, or antibodies against said six CBVs. The antibody-mediated cross-reactivity found between the CBVs is believed to induce a synergistic effect in such a pan-CBV vaccine.

The forms of the CBVs present in the vaccine are independent from each other. For example some of the CBVs may be present in inactivated form and others as components e.g. as virus like particles (VLPs) or as subunits. Conveniently all the CBVs present in the vaccine are in the same form, e.g. inactivated, subunits, VLPs, nucleic acids or antibodies.

A "vaccine" is considered to be a composition capable of providing a protective immune response in the recipient. The vaccine may either elicit an active immune response i.e. it induces a protective immune response in the recipient, or it may provide a passive immune response, i.e. it already contains antibodies needed to prevent or treat the disease.

The vaccine is administered in a "pharmaceutically effective amount" meaning an amount, which is able to elicit an immune response that protects the vaccine recipient against the enterovirus either by eliciting neutralizing antibodies or a cell-mediated response, or both. In case of antibodies a pharmaceutical effective amount is one that mediates a protective immune response against the virus.

The vaccine may contain the virus in "inactivated" form, which means that the infectivity of the virus has been destroyed. The term as used herein also includes viruses that are replication defective. A replication defective virus is a virus defective for a constitutive protein. Such a virus can enter the cell, deliver the partial genome, translate the proteins encoded and replicate the genome but cannot encapsidate new particles. Thus it cannot spread to neighboring cells or tissue.

In case the vaccine comprises a component of the virus, the "component" may be an immunogenic structure of the virus such as a subunit thereof including a chimeric subunit, or a nucleic acid fragment such as part of the genome of the virus. The component may also be recombinantly or synthetically produced or modified.

Thus the vaccine may include whole viruses, the infectivity of which has been inactivated, or subunit vaccines containing certain antigenic structures, proteins or peptides of the virus, or their combination (such as virus like particles), or fragments of viral RNA or cDNA encoding the whole virus or individual viral proteins or inactivated forms of the virus.

Inactivated vaccines may be produced by propagating the virus in cell cultures and by purifying it from infected cells and culture media by high-speed centrifugation in a density gradient formed by sucrose or other high-density media. Alternatively the virus may be purified by chromatography. The infectivity of the purified viruses is destroyed by inactivating the viruses by chemical treatment (e.g. formalin inactivation like that used to produce inactivated polio virus vaccine), irradiation or heat treatment. Replication defective viruses may be prepared by physical or genetic inactivation e.g. by deleting a structural gene in the viral genome, and producing a complementing cell line constitutively expressing the protein encoded by the gene deleted in order to replicate the defective virus.

Subunit vaccines may consist of purified viral proteins or recombinant viral proteins, synthetic peptides corresponding to viral antigenic epitopes, virus like particles or empty viral capsids, which are produced during infection but lack the viral genome. These subunit vaccines can be administered either as such or conjugated to haptens or carriers (e.g. ISCOM particles, chitosan, TLR agonists, biodegradable microparticles).

In case the vaccine comprises an antibody against at least one of said enteroviruses, the antibody may be raised against the whole virus or against an immunogenic component thereof, or it may be recombinantly produced. The term antibody as used herein includes whole antibody molecule of any isotype or fragments of antibodies such as Fab-fragments and scFv fragments.

The above mentioned vaccines can be given parenterally by injections (e.g. intramuscularly or subcutaneously), perorally, intradermally, transcutaneously, sublingually, intranasally, as inhalation, or per rectum. Each immunizing dose includes viral structures in a titer, which is able to induce proper immune response in humans. This dose would correspond to that used in Salk-type inactivated poliovirus vaccine including 1.8-2 μg of viral protein per each dose and 20-40 antigenic D-units of poliovirus type 1,4-8 antigenic D-units of poliovirus type 2 and 16-32 antigenic D-units of poliovirus type 3. The dose may also be another, if it has been confirmed to be safe and immunogenic or able to stimulate the immune system.

The enteroviruses, their components or antibodies can be given in different combinations including one or more enterovirus serotypes given simultaneously or serially. If the different enteroviruses, their components or antibodies are given simultaneously the pharmaceutical composition is in the form of a mixture of different enteroviruses, their components or antibodies.

The enteroviruses, their components or antibodies are used in the manufacture of a vaccine against T1D. They are formulated into a pharmaceutical composition, which in addition to the active ingredients that elicit immune stimulation may comprise pharmaceutically acceptable excipients, carriers, haptens and/or adjuvants. Excipients, carriers, haptens and adjuvants may include for example phenoxyethanol, magnesium chloride, sucrose, thiomersal, formaldehyde, phenol, antibiotics (preservatives) or aluminium salts, polymer microparticles, ISCOM particles, carrier proteins (e.g. cholera toxin), liposomes, protein micelles (haptens/adjuvants), or TLR agonists.

The pharmaceutical composition is preferably administered to a child within 5 years after birth, and more preferably within 3 years, especially within 2 years, and most preferably within 1 year after birth, with boosters given later in life to prevent or treat T1D. It can for example be given at the age or 3, 6 or 12 months, with boosters at older age. It can also be given to pregnant mothers to prevent T1D in the baby, or prenatally to the pregnant mother and postnatally to the baby. When given to pregnant mothers the induced antibody response protects the child because IgG class maternal antibodies are transferred to the fetus through the placenta and are thus protecting the child until the age of 6-12 months when maternal antibodies disappear from the child's circulation. In addition, these protective antibodies are transferred by breast-milk to the breastfed baby. These maternal antibodies, especially breast milk antibodies, have been shown to protect against enterovirus infections in young infants (Sadeharju K, Knip M, Virtanen S M, Savilahti E, Tauriainen S, Koskela P, Akerblom H K, Hyöty H; Finnish TRIGR Study Group. Maternal antibodies in breast milk protect the child from enterovirus infections. Pediatrics. 2007 May; 119(5):941-6.) The vaccination regime can be used in the whole population or in subpopulations carrying increased risk for T1D. Such high-risk groups may include mothers or children with HLA-conferred disease susceptibility to T1D, especially carriers of the HLA DR3 and/or DR4 alleles, subjects with type 1 diabetes in first or second-degree relatives or children testing positive for two or more diabetes-associated autoantibodies.

The vaccines described may be used in preventing and treating type 1 diabetes, in inducing an immune response against CBVs, and in eliminating the diabetogenic effect of CBVs in a subject in need thereof by vaccinating the subject with the pharmaceutical compositions described. The viruses are conveniently administered in inactivated form, as subunits, as virus like particles (VLPs), or as nucleic acids. The prevention and treatment also encompasses use of the vaccine in preventing the progression of prediabetes into diabetes, i.e. preventing infection, or eradication of an ongoing infection in autoantibody-positive children.

If not otherwise indicated "type 1 diabetes" or "T1D" as used herein refers to the classic form of the disease, which is associated with the appearance of autoantibodies against pancreatic beta-cells. This disease may also be called "classic type 1 diabetes" to be distinguished from "fulminant type 1 diabetes", which is a form of diabetes that is associated with a macrophage dominated inflammatory process, which does not involve autoimmune antibodies.

Type 1 diabetes can be prevented or treated by antiviral treatment. This treatment may be, for instance, RNA interference based on a siRNA method, a pharmaceutical preventing the growth of the CBVs, an antibody against the CBVs or its component, or a molecule preventing the virus from adhering to the cell, such as a soluble cell receptor, or it may be a vaccine against the CBVs. These treatments may prevent the development of a T1D disease or treat a disease that has already developed. A person in need of treatment or prevention is given an "anti-coxsackie B virus composition", which is a composition containing an effective amount of a pharmaceutically active anti-CBV substance and pharmaceutically acceptable carrier. The anti-CBV substance may be a virus medicament, such as a chemical drug, a cytokine such as interferone-alpha or interferone-beta, siRNA or a peptide that prevents the interaction between the virus and the receptor, or a soluble receptor molecule, or anti-CBV antibodies.

The invention is illustrated by the following non-limiting examples.

EXAMPLE 1

Seroneutralization Analyses

Neutralizing antibodies were analyzed against a wide panel of different enterovirus serotypes in the same serum sample which was the first autoantibody positive sample taken during the prospective follow-up. Thus, this time point represents the initiation of the beta-cell damaging process. In addition, antibodies against those serotypes which were found to be interesting in this initial screening were measured at additional time-points to study the timing of infections and their relationship with the initiation of the beta-cell damaging process.

Altogether, seroneutralization analyses have been performed using 42 viruses and 522 serum/plasma samples (174 triplets, two control children for each case child). The completeness of the analyses in this virus set varies from 100% to 84% (Echo30) being for a majority of the viruses (35/40) more than 97.7%. In order to study the effect of the strain variation, two serotypes (CBV4 and Echo3) have been analyzed using both the freshly isolated wild type strains (wt) and corresponding reference (ATCC) strains (rs).

The viruses were analyzed in seroneutralization analyses using autoantibody seroconversion date samples. The viruses were CAV4, CAV5, CAV10, CAV16, EV71, CAV9, CBV1, CBV2, CBV3, CBV4-wt, CBV4-rs, CBV5, CBV6, Echo1, Echo2, Echo3-wt, Echo3-rs, Echo4, Echo5, Echo6, Echo7, Echo9, Echo11, Echo12, Echo13, Echo14, Echo15, Echo17, Echo18, Echo19, Echo20, Echo21, Echo25, Echo26, Echo27, Echo29, Echo30, Echo32, Echo33, EV74, EV78 and EV94.

The seroneutralization analyses were mainly carried out using a plaque neutralization assay. In this analysis the ability of the serum/plasma to inhibit a certain virus's ability to form plaques in cell layers has been determined as compared to controls, in which fetal calf serum has been used instead of human serum. In the analysis the inhibition has been considered to be significant (positive result, ++) when it has been more than 85%. The inhibition range between 85-75% has been considered as weaker positive (+) and inhibition of less than 75% has been judged as a negative result. Because these analyses have been performed using two different serum/plasma dilutions (¼ and ¹⁄₁₆) the results have been combined using the classification shown below. A minority of the analyses (such serotypes that did not form plaques) has been carried out using microneutralization analysis, in which the ability of the virus to kill cells can be monitored by CPE and via crystal violet vital staining. Similar classification was used for the results of microneutralization assay as for plaque inhibition assay.

| Class | 1:4 | 1:16 |
|---|---|---|
| Max positive (0) | ++ | ++ |
| Highly positive (1) | ++ | + |
| Moderately positive (2) | ++ | − |
| Positive (3) | + | − |
| Negative (4) | − | − |

Seroneutralization Results

The raw data was exported to Stata package and analyzed using conditional logistic regression models to evaluate the risk of certain serotypes to cause T1D. The results of the conditional logistic regression analysis are given as odds ratios (ORs). If the OR in certain analysis is higher than 1 and the lower limit of the confidence interval (CI at the level of 95%) remains above 1 the virus can be considered as conferring risk for T1D. On the other hand, if both the OR and the higher limit of the 95% CI are below 1, such a serotype appears protective against T1D. In such cases where OR is either over or below 1 and also the 95% CI includes values on both side of 1, the result is not statistically significant (P>0.05). In Table 1 the OR and CI values for CBV1, CBV3 and CBV6 are presented.

TABLE 1

The OR and CI values of CBV1, CBV3 and CBV6. The statistically significant results are bolded.

| Virus | [OR (CI)] 0-3 vs. 4 | [OR (CI)] 0-1 vs. 2-4 | [OR (CI)] 0-2 vs. 4 | [OR (CI)] 0-1 vs. 4 |
|---|---|---|---|---|
| CBV1 | 1.50 (1.02-2.23) | 1.10 (0.65-1.87) | 1.56 (0.94-2.58) | 1.39 (0.68-2.85) |
| CBV3 | 0.39 (0.18-0.82) | 0.56 (0.24-1.34) | 0.36 (0.15-0.85) | 0.50 (021-1.20) |
| CBV6 | 0.64 (0.41-0.97) | 0.57 (0.21-1.59) | 0.86 (050-1.51) | 049 (0.16-1.57) |

The prevalence of antibodies (percentage of children having neutralizing antibodies against each virus serotype) was also calculated. FIG. 1 shows the results of the CBV-subset. The data represent the whole cohort. Classes 0-3 vs. 4, ORs are shown in the upper panel, and seroprevalence in the lower panel. Statistically significant results are marked with circles.

It was found that CBV1 is a clear risk serotype for T1D, while CBV3 and CBV6 appear protective. This association was first drawn from seroneutralization results of a single cross-sectional time-point representing the first autoantibody positive sample, and were later confirmed in multi-time point analyses in which the timing of infections was analyzed in more detail. In these multi-time-point analyses the clearest result was the strong association of the CBV1 risk effect to the six month time window immediately preceding the first detection of type 1 diabetes related autoantibodies.

Multi-Time Point Seroneutralization Analysis with CBV1

To study the temporality of CBV1 infection with respect to AAB appearance, the following time points were selected for the seroneutralization analyses:
   12 months before autoantibody seroconversion
   6 months before autoantibody seroconversion
   point (first detection of autoantibodies; these samples were analyzed previously)
   12 months after autoantibody seroconversion
   Time of the diagnosis of type 1 diabetes According to this plan approximately 1 250 new samples fulfilling the criteria above were identified, collected, anonymized and tested.

All samples were screened using ¼ and 1/16 serum dilutions. In this report the class comparison 03-vs. 4 and sensitivity analyses 1 and 2 has been generally utilized, except in the tight criteria analyses (explained below) in which infections were diagnosed by subjective judgments done by two independent researchers on the basis of pre-fixed criteria listed below for acute infection:

The acute infection was diagnosed according to following criteria, which had to be true for a classified infection:
   A seroconversion from titer 0 to titer 4 or higher
   The titer is 16 in at least one of the following samples
   All follow-up samples remain positive
   All analyses were done blindly without knowing the case-control status of the child.

Antibodies to islet cells were detected by indirect immunofluorescence, and antibodies to insulin, glutamic acid decarboxylase, and protein tyrosine phosphatase-like protein (IA-2) were determined with specific radiobinding assays from a serum sample using standard methods. If two of these four autoantibodies were detected, the subject was considered autoantibody positive (Näntö-Salonen et al., 2008. Lancet 372:1746-1755).

Multi-Time Point Statistical Analyses

All statistical analyses presented are based on conditional logistic regression analyses. Three types of analyses were carried out for this data set. The timing of infections was determined and the time-relationship between infections and appearance of autoantibodies was analyzed. In other words, the frequency of infections among case children were compared to that in control children in each time window separately. The new time point results were analyzed similarly as described above by comparing cases and controls in each time point separately. These analyses were carried out in the whole group and in different subgroups according to the following list:
   Total data set from the whole cohort
   Gender
   Age
   HLA genotype
   Residence area
   Combinations of different AABs in certain follow-up samples
   Diagnosis of diabetes Seroneutralization analyses of these three viruses have been carried out using a plaque neutralization assay as described above.

Statistical analyses in loose and middle criteria approaches were done according to combined classes 0-3 vs. 4 and also sensitivity analyses, in which class 3 (sensitivity analysis 1) or both classes 2 and 3 (sensitivity analysis 2) are removed from the data set, were utilized. In the tight criteria approach the sensitivity analyses were not done due to its intrinsic "sensitivity" character.

Timing of the Infections

The timing of infections caused by CBV1 and the other five related serotypes was approached in the following way: First, the recognized infections were categorized to different time windows relative to the date of seroconversion to autoantibody positivity (AAB+ date). The used windows were as follows:
0. No infections or infection after the AAB+ date
1. Infection more than 12 months before the AAB+ date
2. Infection between 12 and 6 months before the AAB+ date
3. Infection within 6 months before the AAB+ date In the loose criteria approach the first positive result was accepted as an infection regardless of the possibility of maternal antibodies or the possibility that results of the later time point samples turn to negative. The middle criteria approach was done similarly, except that those results that were biased by the identified maternal antibodies were nullified. This judgement were done by two independent experts who evaluated the data carefully and discarded those results in which the maternal antibodies could be the cause of the positivity. In the tight criteria approach the similar judgement procedure were applied. In short the acute infection according to tight criteria were as follows:

a seroconversion from titer 0 to titer 4 or higher
the titer is 16 in at least one of the following samples
all follow-up samples remain positive In addition to using these time-windows separately, analyses were also performed by combining some of these windows together.

Data is shown for the two serotypes (CBV1 and CBV2) identified to be at-risk. The timing of infections caused by the CBV1 risk serotype in these time windows is summarized in Tables 2 and 3. These analyses were done using the loose criteria and middle criteria and the risk effect of infection was analyzed by comparing its frequency in different time-windows to that in window zero (see above). The basic statistical analyses i.e. classes 0-3 vs. 4 and sensitivity analyses 1 and 2 were done.

TABLE 2

CBV1 timing conditional logistic regression analysis, other windows vs. window 0. Loose criteria approach with classes 0-3 vs. 4 and sensitivity analyses 1 and 2.

| CBV1 | Odds ratio | P-value | 95% Conf. Interval | |
|---|---|---|---|---|
| Class 0-3 vs. 4 | | | | |
| Over 12 months before AAB+ date | 1.77 | 0.064 | 0.97 | 3.25 |
| 12-6 months before AAB+ date | 2.24 | 0.007 | 1.25 | 4.00 |
| 6-0 months before AAB+ date | 3.56 | <0.001 | 1.92 | 6.62 |
| Sensitivity 1, Class 0-2 vs. 4 | | | | |
| Over 12 months before AAB+ date | 0.89 | 0.724 | 0.46 | 1.72 |
| 12-6 months before AAB+ date | 1.25 | 0.468 | 0.68 | 2.31 |
| 6-0 months before AAB+ date | 2.19 | 0.018 | 1.15 | 4.17 |
| Sensitivity 2, Class 0-1 vs. 4 | | | | |
| Over 12 months before AAB+ date | 1.19 | 0.684 | 0.51 | 2.79 |
| 12-6 months before AAB+ date | 0.98 | 0.950 | 0.47 | 2.03 |
| 6-0 months before AAB+ date | 2.09 | 0.067 | 0.95 | 4.59 |

TABLE 3

CBV1 timing conditional logistic regression analysis, other windows vs. window 0. Middle criteria approach with classes 0-3 vs. 4 and sensitivity analyses 1 and 2.

| CBV1 | Odds ratio | P-value | 95% Conf. Interval | |
|---|---|---|---|---|
| Class 0-3 vs. 4 | | | | |
| Over 12 months before AAB+ date | 1.62 | 0.262 | 0.70 | 3.75 |
| 12-6 months before AAB+ date | 0.77 | 0.417 | 0.41 | 1.44 |
| 6-0 months before AAB+ date | 2.09 | 0.002 | 1.32 | 3.33 |
| Sensitivity 1, Class 0-2 vs. 4 | | | | |
| Over 12 months before AAB+ date | 1.14 | 0.795 | 0.41 | 3.17 |
| 12-6 months before AAB+ date | 0.66 | 0.307 | 0.30 | 1.46 |
| 6-0 months before AAB+ date | 2.10 | 0.007 | 1.23 | 3.57 |
| Sensitivity 2, Class 0-1 vs. 4 | | | | |
| Over 12 months before AAB+ date | 0.70 | 0.629 | 0.16 | 3.02 |
| 12-6 months before AAB+ date | 0.36 | 0.078 | 0.11 | 1.12 |
| 6-0 months before AAB+ date | 1.44 | 0.342 | 0.68 | 3.05 |

Interestingly, in these analyses the CBV1 infections are clearly found more often in case children according to risk hypothesis with infections occurring close to the time of autoantibody seroconversion (at the time window 6-0 months before the AAB+ date). The result is same in all analyses, except that in sensitivity analysis 2 the statistical significance is missed. Because in this analysis we have accepted all positive antibody results (probably including false positive findings), except maternal antibodies in middle criteria analyses, it is essential to compare these results to those obtained using tight criteria for infections (Table 4).

TABLE 4

CBV1 timing conditional logistic regression analysis, other windows vs. window 0. Tight criteria approach.

| CBV1 | Odds ratio | P-value | 95% Conf. Interval | |
|---|---|---|---|---|
| Over 12 months before AAB+ date | 0.67 | 0.455 | 0.24 | 1.89 |
| 12-6 months before AAB+ date | 1.38 | 0.491 | 0.55 | 3.46 |
| 6-0 months before AAB+ date | 3.76 | 0.001 | 1.68 | 8.44 |

Figure 2:
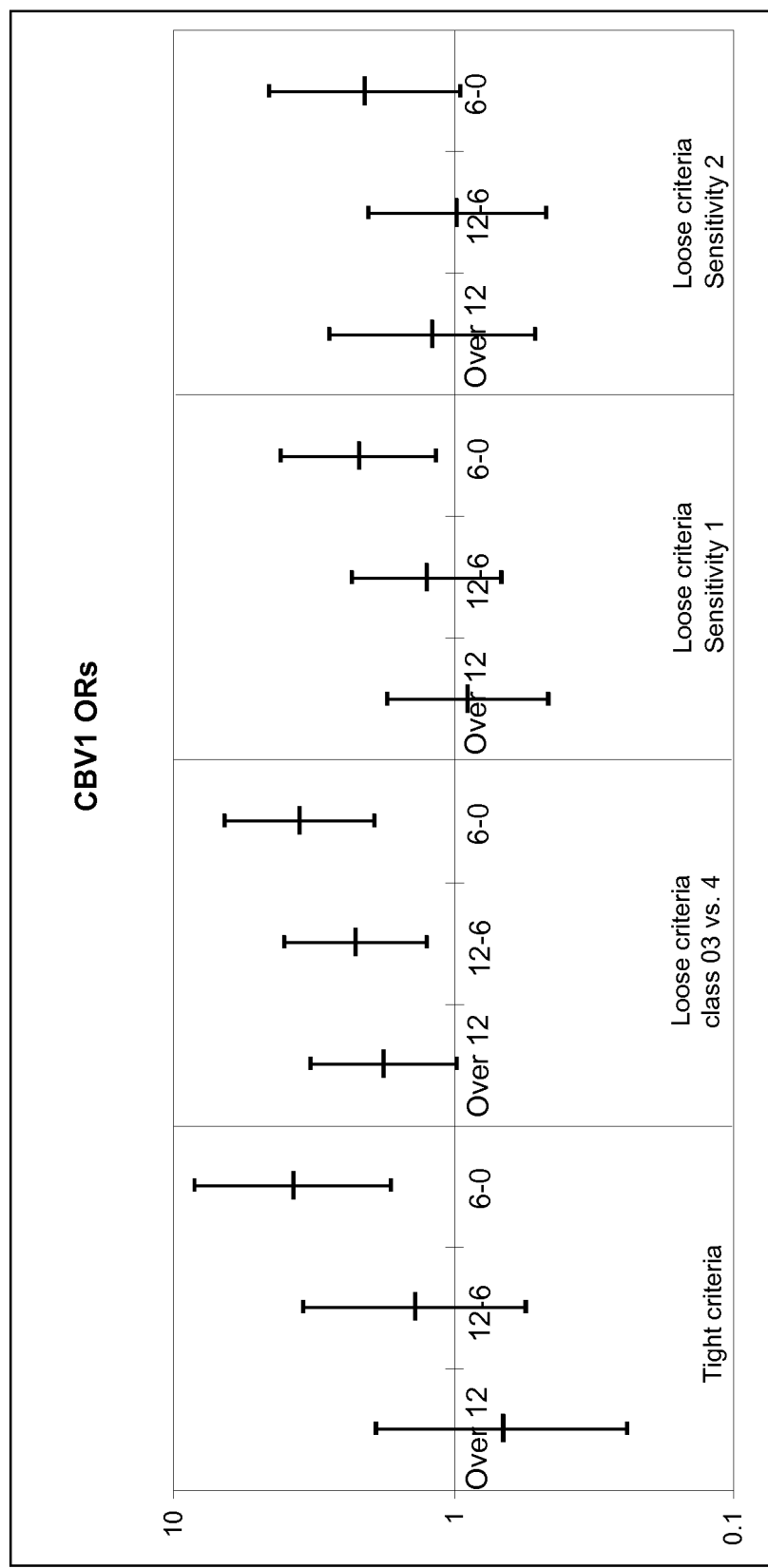
FIG. 2 shows a summary of the tight and loose criteria CBV1 time window analyses.

In this analysis, a lot of data have been removed to exclude all possible wrong positives. The results show that a credible dose response curve is observed highlighting the importance of the time window 6-0 months before the AAB+ date and proving a definite risk effect of CBV1 with convincing statistical outcome. Most importantly, because the same 6-0 months before the AAB+ date window was observed to be statistically significant in both the loose, middle and tight criteria approaches, these results cement this time period as a critical one for the CBV1 infection as a risk to induce T1D. The tight criteria and loose criteria results are presented together in FIG. 2, which shows CBV1 ORs in different time windows before AAB+ date, Left: tight criteria, Right: loose criteria (class 0-3 vs. 4, sensitivity 1, sensitivity 2). The dose response curves can be seen with both approaches being the most conspicuous in the tight criteria and loose criteria sensitivity 1 analyses.

Figure 3:
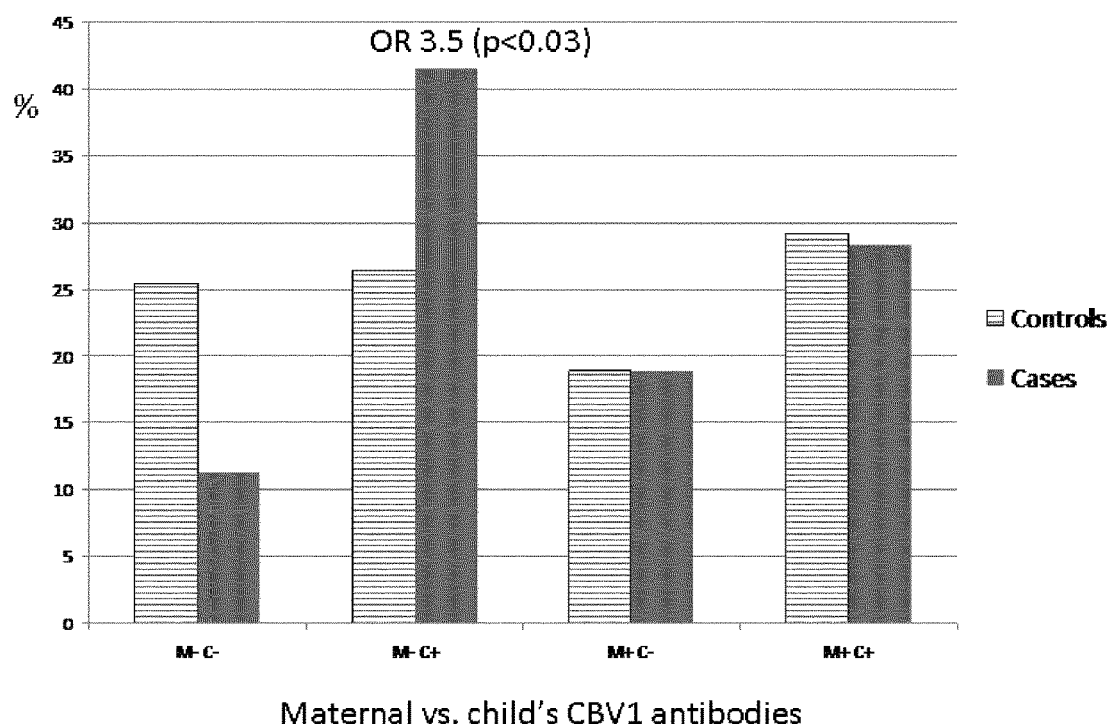
FIG. 3 shows the high risk of beta-cell autoimmunity in children aged 1.5 years, who experience CBV1 infection in the absence of maternal antibodies.

In one analysis we looked at the antibody responses of children aged 1.5 years. In addition to the 1.5 year sample, also the cord blood samples were analyzed to study if the children had got protective antibodies passively from their mothers. In this analysis it was found that if the child was not protected by maternal antibodies and she/he got a CBV1 infection within 1.5 years from birth, the risk effect of CBV1 was extremely clear (OR=3.5, P<0.03) as shown in FIG. 3. This analysis was done using classification 0-3 vs. 4.

Figure 4:
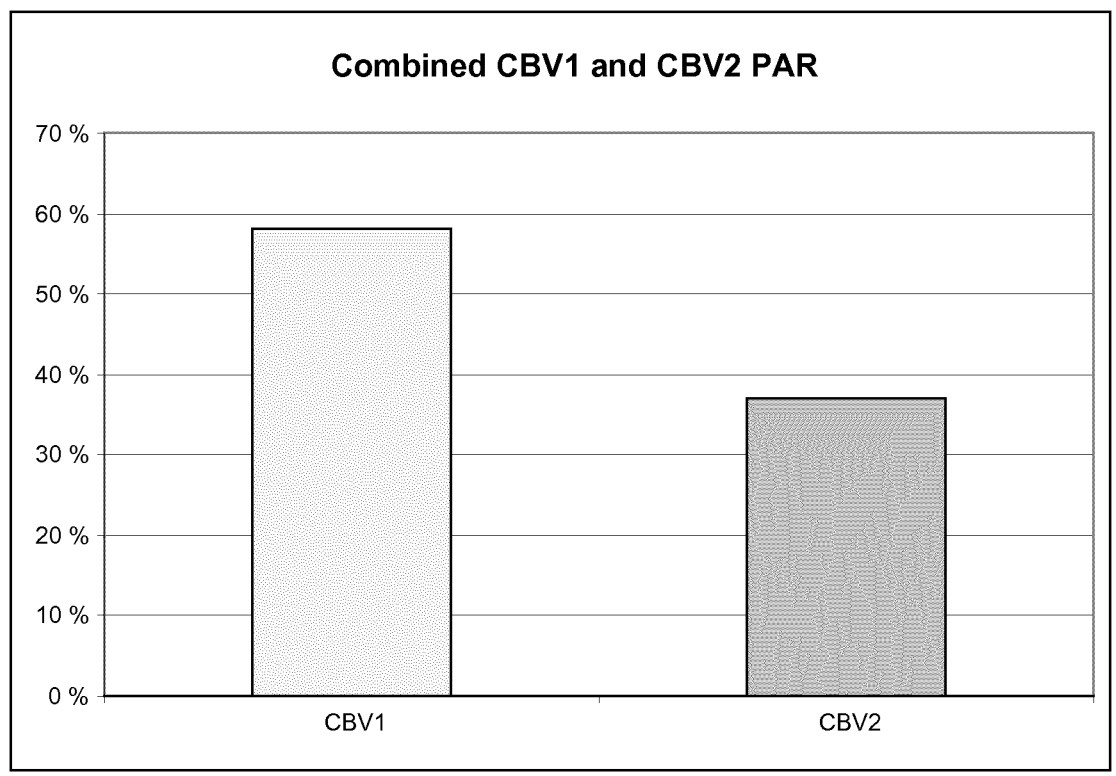
FIG. 4 shows a combined population attributable risk (PAR) for CBV1 and CBV2.

In order to understand the significance of this result let us interpret it in the terms of the population attributable risk (PAR) which estimates the proportion of type 1 diabetes cases which could be prevented by the CBV1 vaccine in the population. Assuming that the OR is 3.76 (=tight criteria result for window 6-0 months before the AAB+ date) and the prevalence of the CBV1 infection is 50% as indicated by the prevalence of CBV1 antibodies in AAB+ time point in control subjects, the PAR equation results in 58% for CBV1 alone (FIG. 4). FIG. 4 shows the population attributable risk (PAR) for CBV1 calculated using an OR of 3.76 and a prevalence (Pc) of 50% representing the seroprevalence at the time of autoantibody seroconversion in control subjects.

In the following analysis the time windows 6-0 and 12-6 were combined. The risk effect of CBV1 was significant also in this combined time window analysis (Table 5).

TABLE 5

CBV1 timing conditional logistic regression analysis, 12-0 window against window 0. Tight criteria approach.

| CBV1 | Odds ratio | P-value | 95% Conf. Interval | |
|---|---|---|---|---|
| Over 12 months before AAB+ date | 0.66 | 0.434 | 0.24 | 1.85 |
| 12-0 months before AAB+ date | 2.46 | 0.004 | 1.33 | 4.53 |

Because the strongest risk effect was seen in the 6-0 window, this time period was analyzed using another type of comparison. Instead of comparing it against window 0 (which was done in the previous analyses), this window was compared to all other windows in combination. Again, the previous findings showing the critical importance of this time-window were supported by this analysis (Table 6).

TABLE 6

CBV1 timing conditional logistic regression analysis, 6-0 window against combined other time windows. Tight criteria approach.

| CBV1 | Odds ratio | P-value | 95% Conf. Interval | |
|---|---|---|---|---|
| 6-0 months before AAB+ date | 3.78 | 0.001 | 1.69 | 8.43 |

Multi-Time Point Seroneutralization Analysis Further Including CBV2

In this analysis also CBV2 serotype was analyzed in similar multi-time-point setting as CBV1.

Timing of Infections

To clarify the possible timing of CBV subgroup infections, the same time points were selected for the seroneutralization analyses as described above.

The results presented below are based on the seroneutralization analysis of about 2 000 samples. In order to study the timing of infections caused by the six CBV serotypes the recognized infections were categorized to different time windows relative to the date of seroconversion to autoantibody positivity (AAB+ date). The used windows were numbered from 0 to 3 as described above.

The same loose, middle and tight criteria approaches were used as described above. Statistical analyses were done using conditional logistic regression. Since some additional laboratory results have been added to the results are shown here also for CBV1. The results of statistical analyses for CBV serotypes are shown in Tables 7-8.

TABLE 7

CBV1 infection timing analysis. Loose criteria approach with classes 0-3 vs. 4.

| CBV1 | Odds ratio | P-value | 95% Conf. Interval | |
|---|---|---|---|---|
| Class 0-3 vs. 4 | | | | |
| Over 12 months before AAB+ date | 1.89 | 0.035 | 1.05 | 3.40 |
| 12-6 months before AAB+ date | 2.27 | 0.005 | 1.28 | 4.03 |
| 6-0 months before AAB+ date | 3.54 | <0.001 | 1.95 | 6.42 |

TABLE 8

CBV2 infection timing analysis. Loose, Middle and Tight criteria approaches with classes 0-3 vs. 4.

| CBV2 | Odds ratio | P-value | 95% Conf. Interval | |
|---|---|---|---|---|
| Loose criteria | | | | |
| Over 12 months before AAB+ date | 0.79 | 0.441 | 0.44 | 1.43 |
| 12-6 months before AAB+ date | 1.38 | 0.236 | 0.81 | 2.34 |
| 6-0 months before AAB+ date | 2.32 | 0.001 | 1.40 | 3.84 |
| Middle criteria | | | | |
| Over 12 months before AAB+ date | 0.80 | 0.523 | 0.41 | 1.58 |
| 12-6 months before AAB+ date | 1.02 | 0.946 | 0.54 | 1.93 |
| 6-0 months before AAB+ date | 2.29 | 0.001 | 1.43 | 3.66 |
| Tight Criteria | | | | |
| Over 12 months before AAB+ date | 0.88 | 0.838 | 0.26 | 3.00 |
| 12-6 months before AAB+ date | 1.00 | 0.994 | 0.33 | 3.03 |
| 6-0 months before AAB+ date | 2.44 | 0.059 | 0.97 | 6.15 |

Conclusions

In addition to CBV1 also the closely related CBV2 was found to be a risk virus in multi-time-point analyses especially in the 6-0 months before AAB+ time window. Thus, the multi-time-point analyses produced a good second candidate for the preventive vaccine.

PAR was also calculated for CBV2 using loose criteria OR=2.26 and the seroprevalence of 48% in background population, accordingly, we end up with PAR=37% (FIG. 4). The result indicates that a vaccine cocktail combination of CBV1 and CBV2 is most interesting. These two viruses can lead to a product having a major effect to prevent the onset of the type 1 diabetes. Altogether, the results indicate that CBV2 is also a risk virus associated with the pathogenesis of T1D and therefore useful in the development of the vaccine.

Multi-Time Point Seroneutralization Analysis Further Including CBV6

In this analysis also CBV6 serotype was analyzed in a similar multi-time-point setting as CBV1 and CBV2. However, in this case, in addition to the whole cohort analysis, the analyses were also done separately for each gender.

Timing of Infections

To clarify the possible timing of CBV subgroup infections, the same time points were selected for the seroneutralization analyses as described above.

The results presented below are based on the seroneutralization analysis of about 2 000 samples. In order to study the timing of infections caused by the CBV serotypes the recognized infections were categorized to different time windows relative to the date of seroconversion to autoantibody positivity (AAB+ date). The used windows were numbered from 0 to 3 as described above.

The same loose, middle and tight criteria approaches were used as described above. Statistical analyses were done using conditional logistic regression. The results of the statistical analyses for CBV6 are shown in Table 9.

TABLE 9

CBV6 infection timing analysis for the whole cohort and separately for females and males. Loose, Middle and Tight criteria approaches with classes 0-3 vs. 4.

| Months before AAB+ | Loose | | 95% Conf. Interval CBV6 | | Middle | | 95% Conf. Interval CBV6 | | Tight | | 95% Conf. Interval CBV6 | |
|---|---|---|---|---|---|---|---|---|---|---|---|---|
| | OR | P | | | OR | P | | | OR | P | | |
| Both gender | | | | | | | | | | | | |
| >12 | 0.96 | 0.87 | 0.56 | 1.65 | 1.19 | 0.58 | 0.65 | 2.16 | 0.67 | 0.62 | 0.13 | 3.3 |
| 12-6 | 1.54 | 0.09 | 0.94 | 2.54 | 1.32 | 0.33 | 0.76 | 2.32 | 0.5 | 0.39 | 0.11 | 2.38 |
| 6-0 | 1.35 | 0.23 | 0.82 | 2.22 | 1.35 | 0.23 | 0.83 | 2.2 | 1.16 | 0.84 | 0.28 | 4.86 |
| Girls | | | | | | | | | | | | |
| >12 | 0.57 | 0.29 | 0.20 | 1.62 | 0.69 | 0.51 | 0.22 | 2.11 | nd | nd | nd | nd |
| 12-6 | 2.14 | 0.06 | 0.96 | 4.77 | 1.39 | 0.47 | 0.57 | 3.39 | nd | nd | nd | nd |
| 6-0 | 2.42 | 0.05 | 1.02 | 5.78 | 2.69 | 0.03 | 1.09 | 6.60 | 2.00 | 0.49 | 0.13 | 32.02 |
| Boys | | | | | | | | | | | | |
| >12 | 1.23 | 0.53 | 0.65 | 2.32 | 1.59 | 0.21 | 0.77 | 3.28 | 1.33 | 0.75 | 0.22 | 7.98 |
| 12-6 | 1.23 | 0.53 | 0.64 | 2.38 | 1.27 | 0.52 | 0.61 | 2.66 | 0.67 | 0.62 | 0.13 | 3.31 |
| 6-0 | 0.99 | 0.97 | 0.53 | 1.85 | 0.96 | 0.89 | 0.52 | 1.76 | 0.97 | 0.97 | 0.18 | 5.32 |

Conclusion

Although CBV6 was generally found as a protective serotype in AAB+ single time point analysis, in multi-time point analyses it showed a trend for risk in the time window 12-6 months before AAB+ time window. Therefore the importance of CBV6 was studied in more detail and the same timing analysis was carried out separately for females and males. The results of this analysis showed that the observed risk trend of the CBV6 in the whole cohort associated strongly with female gender in both time windows 12-6 months and 6-0 months before AAB+ time window. In contrast, for males there was no evidence of CBV6 associated risk. So, in overall, CBV6 may appear as a protective serotype, but when a certain subcohort, such as the females, is analyzed, it can turn into a risk virus in a said subcohort.

EXAMPLE 2

A CBV1 Inactivated Vaccine Protects Mice Against Viremia and Infection of the Pancreas Method An inactivated vaccine was produced by amplification of CBV1 in Vero cells, followed by sucrose purification and formol-inactivation. The dose of the vaccine is expressed as the initial content in infectious virus (equivalent $CCID_{50}$).

BALB/c male and female mice, previously shown to be susceptible to CBV1 infection, were immunized by the i.m. route with three injections of formol-inactivated CBV1 at D0, D21 and D35. Two doses of the vaccine ($4 \times 10^4$ and $2 \times 10^5$ eq $CCID_{50}$) were assessed for mice immunization. One week after the last immunization, mice were challenged with live CBV1 via the i.p. route. Viremia and infection of the pancreas were monitored in immunized and control mice by CBV1 genomic titration of blood samples and pancreas tissue homogenates.

Results

Immunogenicity of the vaccine was first evaluated by analyzing the induction of neutralizing antibodies in individual mouse. The mean values obtained for each group of 5 mice are reported in Table 10.

Neutralizing antibodies were detectable in all immunized groups after 2 injections (D35) whatever the vaccine dose used for immunization. After completion of the 3 vaccine administrations, all immunized mice showed detectable neutralizing antibodies titers when using the $2 \times 10^5$ eq $CCID_{50}$ vaccine dose.

TABLE 10

An inactivated CBV1 vaccine induces consistent neutralizing antibodies in mice

| Vaccine dose (eq $CCID_{50}$) | | Neutralizing antibody titers | | | |
|---|---|---|---|---|---|
| | | D2 | D21 | D35 | D42 |
| ♂ | $4 \times 10^4$ | <1/20 | <1/20 | 1/20 | 1/44 |
| | $2 \times 10^5$ | <1/20 | <1/20 | 1/24 | 1/44* |
| | PBS (naive) | <1/20 | <1/20 | <1/20 | <1/20 |
| ♀ | $4 \times 10^4$ | <1/20 | <1/20 | 1/24 | 1/144 |
| | $2 \times 10^5$ | <1/20 | <1/20 | 1/28 | 1/76* |
| | PBS (naive) | <1/20 | <1/20 | <1/20 | <1/20 |

*all mice responding

The protective effect of the vaccine was then assessed after a challenge with live CBV1 administered at an infectious dose previously shown to induce a marked viremia at D2 and replication of the virus in pancreas up to D7.

Figure 5:
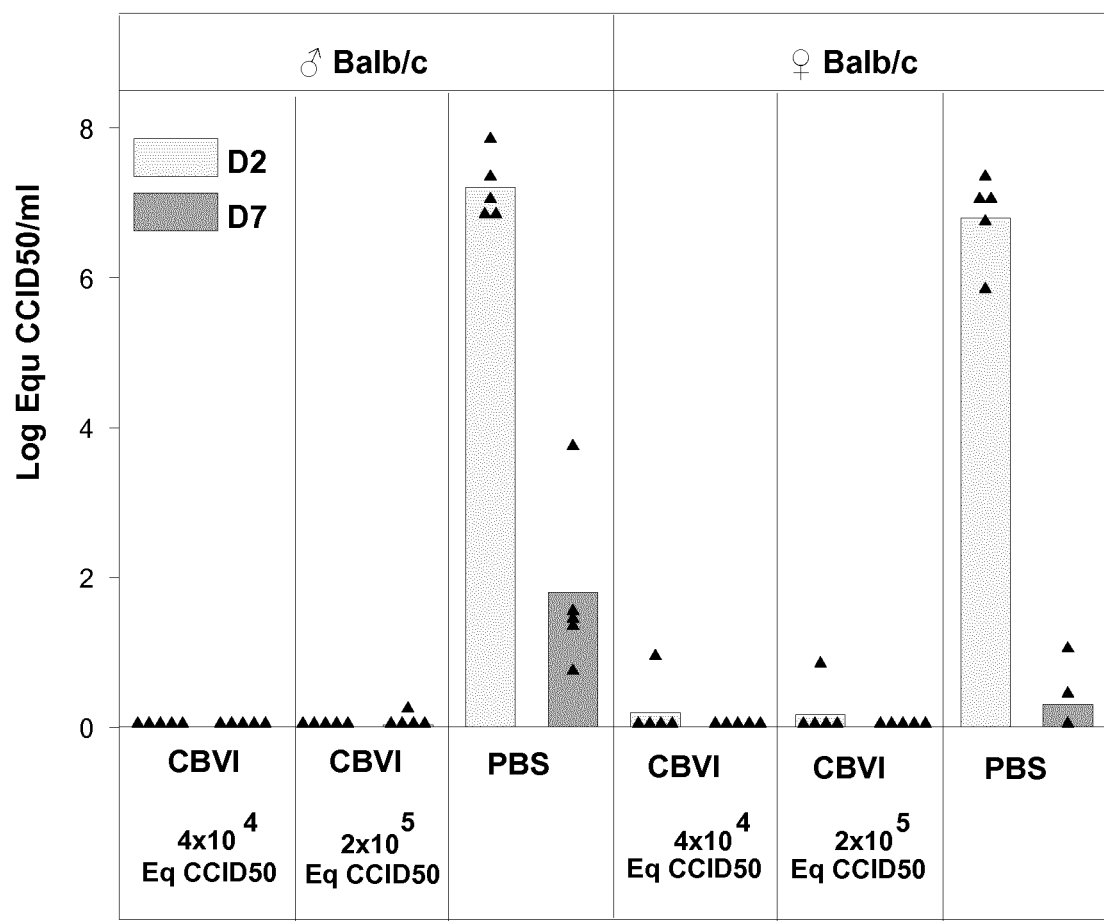
FIG. 5 shows viremia in vaccinated and unvaccinated mice on Day 2 and Day 7 post challenge with live CBV1 with dose of $10^4 CCID_{50}$ administrated via ip route.
Figure 6:
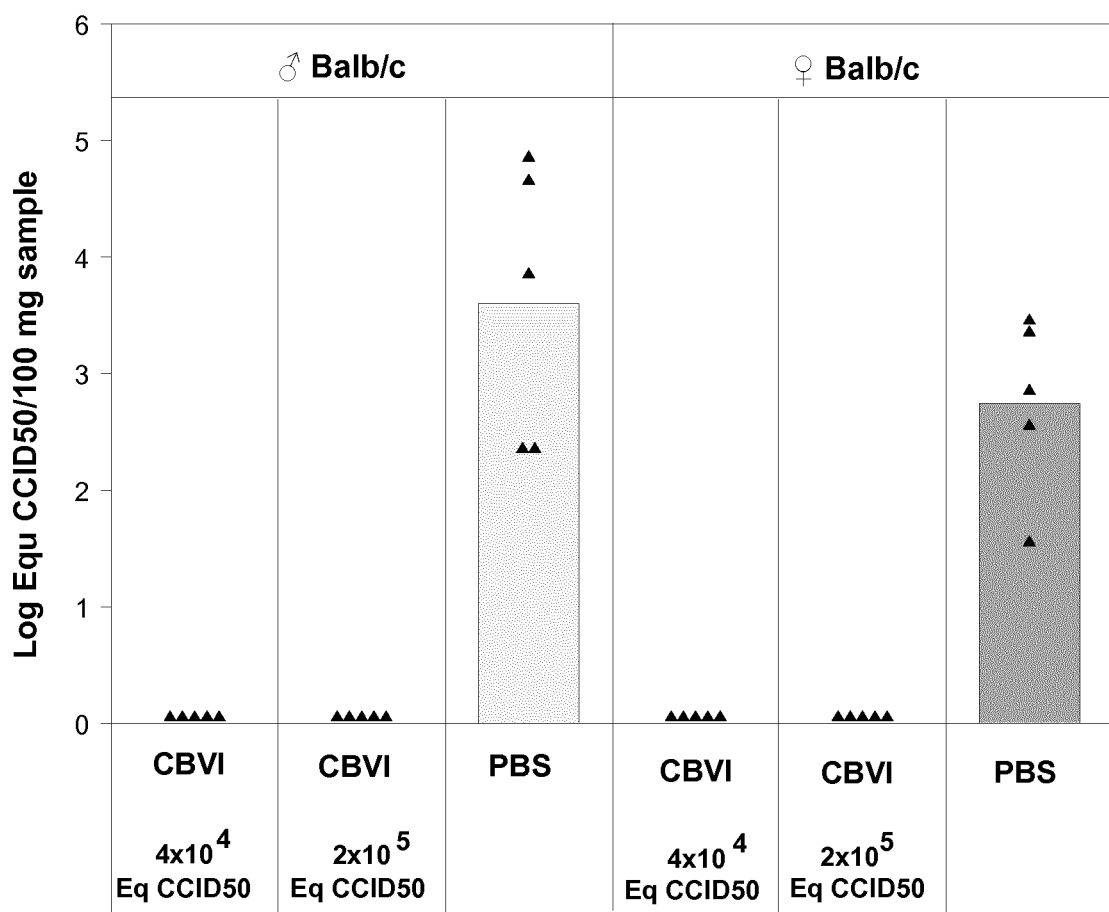
FIG. 6 shows virus quantification in pancreas in vaccinated and unvaccinated mice on Day 7 post challenge with live CBV1 with dose of $10^4 CCID_{50}$ administrated via ip route.

In contrast to naive mice, all immunized mice were protected from CBV1 infection as demonstrated by the absence of detectable virus in blood (FIG. 5) and in pancreas (FIG. 6) in the days following the ip challenge.

Conclusion

The inactivated CBV1 vaccine protects against viremia and viral replication in the pancreas caused by live CBV1. As induction of autoimmunity following infection has been related to the inflammation caused by viral replication (ref Horwitz et al, Nat Med 1998; Zipris Clin Immunol 2009;), the CBV1 vaccine can protect from CBV1-induced autoimmunity.

EXAMPLE 3

Virus Infection and Diabetes in SOCS-1 Transgenic NOD Mice

A recently developed model for enterovirus-induced type 1 diabetes was used with mice expressing the suppressor of cytokine signaling-1 (SOCS-1) in pancreatic beta cells. By expressing SOCS-1 the pancreatic beta cells lose their ability to respond to interferons and by that also their ability to protect themselves against the virus. An analysis of the pancreata from infected SOCS-1 transgenic animals (here denoted SOCS-1-Tg NOD mice) demonstrate that diabetes is the result of beta cell destruction (Flodstrom, M. et al., 2002. Nat Immunol 3(4), 373-82; Flodstrom, M. et al., 2003.Diabetes 52(8), 2025-34).

Mice and animal husbandry:

All mice were breed and housed under specific pathogen free conditions. The SOCS-1-Tg NOD mice were bred as heterozygotes and screened for the presence of the SOCS-1-transgene by PCR.

Virus Infections

Mice aged 8 to 10 weeks were infected with one intraperitoneal (i.p.) injection of CBV1 ($10^1$, $10^3$-$10^8$, and $4 \times 10^8$ CCID50/animal). Weight and venous blood glucose measurements were done on non-fasting mice with 1-2 days intervals during the acute phase of the infection (app. day 3-12 p.i) and thereafter on a weekly basis. Animals were considered diabetic when having two consecutive blood glucose measurements >13 mM. Diabetic animals were sacrificed on the same day as the second reading was made. All non-diabetic animals were followed up to at least 21 days post infection (p.i.). Pancreata were retrieved upon sacrifice and were fixed in 4% formalin for histology.

Histology and Immunohistochemistry:

Paraffin sections (4 μm) were made from selected pancreata and stained with hematoxylin and eosin (H&E) or with guinea pig anti-insulin or rat anti-glucagon primary antibodies (DAKO Cytomation, Stockholm, Sweden), as previously described in e.g. (Flodstrom et al., 2002 supra).

Summary of Obtained Results

According to plan, SOCS-1-Tg NOD mice were challenged with different doses of CBV1 ($10^1$, $10^3$-$10^8$, and $4 \times 10^8$ CCID50/animal). The infections were well tolerated with no or minor effects on animal weights. Some SOCS-1-Tg NOD mice became diabetic rapidly after infection, with the highest incidence (50%) obtained with the dose $4 \times 10^8$ CCID50/animal (Table 11).

A histological analysis of selected pancreata demonstrated that mice that developed diabetes had lost most, but not all, of their beta cell mass. Some islet completely lacked insulin-positive cells while others still contained cells positively stained with the insulin-antibody.

Conclusions and Comments

CBV1 triggered diabetes in SOCS-1-Tg NOD mice although disease penetrance was at most 50% ($4 \times 10^8$ CCID50/animal, n=2). Diabetes appeared, at least in part, to be the result of a destruction of the pancreatic beta cells as animals that had developed diabetes had islets either lacking insulin-positive beta cells or islets with lower than normal numbers of insulin-positive cells. The islets in SOCS-1-Tg NOD mice that did not develop diabetes appeared normal, some with surrounding lymphocyte infiltrates that are commonly seen in SOCS-1-Tg and non-Tg NOD mice at this age.

TABLE 11

Incidence of diabetes in CBV1 infected SOCS-1-Tg NOD and NOD mice

| Virus dose (CCID50/-animal) | SOCS-1-Tg NOD mice | | | |
| --- | --- | --- | --- | --- |
| | Diabetic animals of total | Diabetic animals (percent) | No. of females | No. of males |
| $10^1$ | 0/6 | 0 | 6 | 0 |
| $10^3$ | 0/5 | 0 | 3 | 2 |
| $10^4$ | 1/6 | 17 | 2 | 4 |
| $10^5$ | 1/7 | 14 | 7 | 0 |
| $10^6$ | 1/8 | 13 | 8 | 0 |
| $10^7$ | 2/7 | 29 | 0 | 7 |
| $10^8$ | 2/5 | 40 | 0 | 5 |
| $4 \times 10^8$ | 1/2 | 50 | 0 | 2 |

EXAMPLE 4

Risk Character of CBV2

In this study altogether 284 serum samples were collected from children at the age of one year (range 321-430 days) and their seroneutralization responses were studied. Seroneutralization results of autoantibody seroconversion date done with six CBV serotypes were compared to results of the samples from type 1 diabetes diagnosis date taken from the same children and using the same viruses. In this analysis the reference group consisted of children who were negative for a given virus in both samples. The results are shown in Table 12. A link between CBV2 infections and risk of type 1 diabetes was detected when the data of interval between autoantibody seroconversion date samples and the samples taken at the date of diabetes diagnosis were compared. CBV2 showed a risk trend with high OR indicating that it may accelerate the autoimmune process progression after its initiation.

TABLE 12

Conditional logistic regression analysis of 6 CBV serotypes. Sample interval between autoantibody seroconversion date and type 1 diabetes diagnosis date were compared. Loose criteria approach: classes 0-3 vs. 4. Changes from negative to positive have been analyzed against reference group negative to negative.

| OR | P | 95% Conf. Interval | |
| --- | --- | --- | --- |
| CBV1 | | | |
| 0.82 | 0.797 | 0.18 | 3.78 |
| CBV2 | | | |
| 6.04 | 0.106 | 0.68 | 53.32 |
| CBV3 | | | |
| 0.78 | 0.778 | 0.14 | 4.36 |
| CBV4 | | | |
| 0.35 | 0.339 | 0.04 | 3.02 |
| CBV5 | | | |
| 0.18 | 0.108 | 0.023 | 1.45 |
| CBV6 | | | |
| 0.89 | 0.813 | 0.35 | 2.27 |

EXAMPLE 5

Antibody Cross-Reactivity within CBV Serotypes

Antibody cross-reactivity within the CBV serotypes was analyzed using the seroneutralization study cohort with two sample series. The antibodies against CBV serotypes were measured in the plaque seroneutralization assay and the serum samples were titrated to their endpoint titer. Samples were analyzed from 23 children having antibodies (titer at least 1/16) against CBV1, CBV3 or CBV6. For the rest of these viruses it was lower but at a detectable level (classes 1-3). The other sample series included eight children having one of the CBV serotypes detected in a stool sample. In all eight children the antibody response was specifically induced with high titers (titer at least 1:512) against the serotype detected in stools. Here the serum sample was collected immediately before or straight after the CBV-positive stool sample and the antibody response remained high in the follow-up samples. When the children selected for these groups were observed as one group a clear tendency was observed. According to this cohort analyses CBV3 showed cross-reactivity with CBV1, CBV2 and CBV6 (Table 13).

TABLE 13

The main trends of the low-titer temporary peaks suggesting cross-reactivity between different CBV serotypes. CBV3 homotypic responses were found in 18 children (from 65 samples) of whom 12 children (in 26 samples) also had low-titer temporary responses in CBV1, CBV2 or CBV6.

| Homotypic response | Low-titer temporary response in | Number of samples where low-titer temporary response | Number of children having low-titer temporary response |
|---|---|---|---|
| CBV3 | CBV1 | 9 | 4 |
|  | CBV2 | 4 | 4 |
|  | CBV6 | 13 | 7 |

Another cross-neutralization assay was performed using monospecific sera raised against CBV1-6 serotypes in monkeys (specific strains produced by the Swedish Institute for Communicable Diseases) and CBV1 and CBV3-6 ATCC-reference strains in horses (purchased from ATCC). Analyses were performed with the CBV virus strains available. The cross-neutralization analyses performed with hyperimmunized monkey sera (antibody set no. 1) showed strong cross-reactivity between CBV4 virus and antisera raised against all other CBV serotypes (Table 14). Further, the CBV1 antiserum cross-reacted weakly with CBV6 and, vice versa, the CBV6 antiserum showed weak cross-reactivity with the CBV1 virus. Another cross-neutralization study performed with the hyperimmunized horse sera (ATCC-sera) showed that the CBV6 antiserum cross-neutralized both CBV1 and CBV3 viruses (Table 15). No reaction vice-versa was observed for CBV1 or CBV3 antisera against the CBV6 virus. No cross-reactivity was seen with CBV4 either, which is in contrast to the results obtained with the antibody set 1.

TABLE 14

The cross-neutralization study performed with the hyperimmunized monkey sera (antibody set no. 1 from the Swedish Institute for Communicable Diseases, Stockholm, Sweden). 75% plaque inhibition is used as a threshold value for inhibition.

| | CBV1 V19 | CBV2 V20 | CBV3 V21 | CBV4 (WT) V22 | CBV4 (ref. strain) V22r | CBV5 V23 | CBV6 V24 |
|---|---|---|---|---|---|---|---|
| CBV1 Antiserum | 1:8000* | NO | NO | 1:2048<br>4** | 1:2048<br>4 | 1:8<br>1000 | 1:16<br>500 |
| CBV2 Antiserum | NO | 1:4000 | NO | 1:8<br>500 | NO | NO | NO |
| CBV3 Antiserum | NO | NO | 1:8000 | 1:2048<br>4 | 1:128<br>62.5 | 1:16<br>500 | NO |
| CBV4 Antiserum | 1:16<br>750*** | NO | 1:4<br>3000*** | 1:8000 | 1:16000 | 1:4<br>3000*** | NO |
| CBV5 Antiserum | NO | NO | NO | 1:2048<br>4 | 1:2048<br>4 | 1:8000 | NO |
| CBV6 Antiserum | 1:4<br>4000 | NO | NO | 1:1024<br>16 | 1:256<br>62.5 | NO | 1:16000 |

*Upper row: Titer with serotype-specific antisera (homotypic response)

**Lower row: How many times the serotype-specific titer is higher than non-specific cross-reactive titer

***For calculating specific over non-specific titer for CBV4 antisera the mean of specific titers from two different CBV4 strains has been used NO = no detected cross-reactivity

TABLE 15

The cross-neutralization study performed with hyperimmunized horse sera (ATCC origin). 75% plaque inhibition is used as a threshold value for inhibition.

| | CBV1 V19 | CBV2 V20 | CBV3 V21 | CBV4 (WT) V22 | CBV4 (ref. strain) V22r | CBV5 V23 | CBV6 V24 |
|---|---|---|---|---|---|---|---|
| CBV1 antiserum | 1:128* | NO | NO | NO | NO | NO | NO |
| CBV3 antiserum | NO | NO | 1:128 | NO | NO | NO | NO |
| CBV4 antiserum | NO | NO | NO | 1:2048 | 1:2048 | NO | NO |
| CBV5 antiserum | NO | NO | NO | NO | NO | 1:2048 | 1:32<br>64** |

TABLE 15-continued

The cross-neutralization study performed with hyperimmunized horse sera (ATCC origin). 75% plaque inhibition is used as a threshold value for inhibition.

|  | CBV1 V19 | CBV2 V20 | CBV3 V21 | CBV4 (WT) V22 | CBV4 (ref. strain) V22r | CBV5 V23 | CBV6 V24 |
|---|---|---|---|---|---|---|---|
| CBV6 antiserum | 1:128 64** | NO | 1:128 64** | NO | NO | NO | 1:8192 |

NO = no detected cross-reactivity
*Upper row: Titer with serotype-specific antisera (homotypic response)
**Lower row: How many times the serotype-specific titer is higher than non-specific cross-reactive titer

EXAMPLE 6

Sequence Analyses

The aim of this study was to identify enterovirus serotypes causing type 1 diabetes by direct sequence analysis from serum samples collected from children who had been followed from birth until they turned positive for diabetes-associated autoantibodies or developed clinical type 1 diabetes. The study was based on serum and plasma samples collected in a prospective birth cohort study, which included two subcohorts of the children. Cohort 1 comprised children who have been screened for enterovirus RNA in previous academic studies carried out at the University of Tampere. The aim was to sequence all enterovirus positive samples detected in this cohort. Cohort 2 included the same children who were screened for neutralizing enterovirus antibodies in the previous study. The aim was to screen these cohort 2 children for the presence of enterovirus RNA in serum and to sequence all virus positive samples.

The sequencing was done with semi-nested RT-PCR using EV group VP1 region specific primers as disclosed in Nix et al., J Clin Microbiol. 2006 August; 44(8): 2698-704, and using EV group VP2 region specific primers as disclosed in Nasri et al. J Clin Microbiol. 2007 August; 45(8): 2370-9.

In these analyses the data from cohort 1 and cohort 2 were combined. This combined cohort included 1629 samples from 241 case children and 4066 samples from 687 control children. Altogether 115 samples were positive for enterovirus including 34 positive samples from the case children and 81 positive samples from the control children (Table 16).

TABLE 16

Number of analyzed (N) and enterovirus positive samples (EV+) of case and control groups in the combined cohort.

| Combined cohort 1 and 2 | Whole follow-up | Birth-AAb | 6 mo window prior Aab | AAb-T1D |
|---|---|---|---|---|
| Case (N) | 4066 | 2668 | 1095 | 914 |
| Control (N) | 1629 | 1006 | 346 | 517 |
| Case (EV+) | 81 | 58 | 18 | 16 |
| Control EV(+) | 34 | 20 | 9 | 9 |

Sequencing analyses targeted to altogether 91 enterovirus positive samples in cohort 1 and 24 enterovirus positive samples in cohort 2. Out of these 115 positive samples, 34 were from case children and 81 from control children. These samples included 25 samples from case children in cohort 1 and 9 samples from case children in cohort 2, as well as 66 enterovirus positive samples from control children in cohort 1 and 15 enterovirus positive samples from control children in cohort 2. Sequence analyses were also done for some samples, which were excluded from statistical analysis of screening PCR results. All enterovirus samples were sequenced from VP1 and VP2 regions which allow the identification of the serotype. Altogether 9 case samples (26%) and 26 control samples (28%) were sequenced successfully. All samples which were successful in both VP1 and VP2 sequencing showed the same serotype in a blast search. In addition, all enterovirus positive samples were sequenced for the 5-NCR sequence amplified by the screening RT-PCR.

The serotype distribution differed clearly between case and control children: In the case children coxsackie B serotypes predominated and coxsackie A serotypes were rare, while in the control children coxsackie A serotypes predominated. Among the case children the CBV viruses represented 44% of all serotypes identified, and among the control children they represented only 19% of all identified serotypes (Table 17). The CBV serotypes identified were CBV3, CBV4 and CBV5 in both groups.

TABLE 17

Proportion (%) of detected enterovirus types divided into two groups: CBV viruses and non-CBV viruses. These results are based on VP1 and VP2 sequencing in the case and control subjects.

| Virus group | Cases | Controls |
|---|---|---|
| CBV (%) | 44 | 19 |
| non-CBV (%) | 56 | 81 |

Conclusion

The predominance of the CBV serotypes in the sera of case children indicates that the CBV group viruses are linked to T1D and play a role in the pathogenesis of the disease. This result together with the strongest endpoint (children progressed to clinical type 1 diabetes in cohort 1), i.e. statistically significant risk of enterovirus infections in the 6 month window before autoantibody seroconversion date, also indicate a causal linkage between the CBV infections and the initiation of the type 1 autoimmune process.

The invention claimed is:

1. A method of inducing an immune response to coxsackie B virus (CBV) in an individual, the method comprising administering to the individual an effective amount of a composition comprising:
   a) CBV1 and CBV2 in inactivated form or in the form of a subunit or a virus-like particle (VLP); and b) at least one CBV selected from CBV3, CBV4, and CBV5, in inactivated form or in the form of a subunit or a VLP, wherein the composition does not include CBV6, wherein the individual is a carrier of an HLA DR3 and/or DR4 allele, and wherein said administering induces an immune response to CBV in the individual.

2. The method of claim 1, wherein the CBVs are inactivated.

3. The method of claim 1, wherein the CBVs are in the form of a subunit of the CBVs.

4. The method of claim 1, wherein the CBVs are in the form of VLPs of the CBVs.

5. The method of claim 1, wherein the composition comprises CBV1, CBV2, CBV3, CBV4, and CBV5 in inactivated form or in the form of a subunit or a VLP.

6. The method of claim 1, wherein the composition comprises a pharmaceutically acceptable excipient.

7. The method of claim 1, wherein the composition comprises an adjuvant.

8. The method of claim 1, wherein the composition is administered intramuscularly.

9. The method of claim 1, wherein the composition is administered subcutaneously.

\* \* \* \* \*